United States Patent
Tegg et al.

(10) Patent No.: US 11,484,690 B2
(45) Date of Patent: Nov. 1, 2022

(54) TORQUEABLE STEERABLE SHEATHS

(71) Applicant: St. Jude Medical, Cardiology Division, Inc., St. Paul, MN (US)

(72) Inventors: Troy Tegg, Elk River, MN (US); Bruce Ebner, Shorewood, MN (US); Cherry Knight, New Hope, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 628 days.

(21) Appl. No.: 15/955,908

(22) Filed: Apr. 18, 2018

(65) Prior Publication Data

US 2018/0296801 A1 Oct. 18, 2018

Related U.S. Application Data (60) Provisional application No. 62/486,725, filed on Apr. 18, 2017.

(51) Int. Cl.
*A61M 25/01* (2006.01)
*A61M 25/00* (2006.01)
*B29C 65/00* (2006.01)

(52) U.S. Cl.
CPC .... *A61M 25/0147* (2013.01); *A61M 25/0012* (2013.01); *A61M 25/0136* (2013.01);
(Continued)

(58) Field of Classification Search
CPC .......... A61M 25/0147; A61M 25/0012; A61M 25/0136; A61M 25/0045; A61M 25/005;
(Continued)

(56) References Cited

U.S. PATENT DOCUMENTS

| 7,691,095 B2 | 4/2010 | Bednarek et al. |
| 7,914,515 B2 | 3/2011 | Heideman et al. |

(Continued)

FOREIGN PATENT DOCUMENTS

| WO | 9414494 A2 | 7/1994 |
| WO | 2017062514 A1 | 4/2017 |

OTHER PUBLICATIONS

International Search Report and Written Opinion for International Patent Application No. PCT/US2018/028110, dated Jul. 6, 2018, 15 pages.

*Primary Examiner* — Bhisma Mehta
*Assistant Examiner* — Nidah Hussain
(74) *Attorney, Agent, or Firm* — Armstrong Teasdale LLP (57) ABSTRACT

A steerable sheath includes an inner liner extending from a proximal end to a distal end of the steerable sheath. The inner liner includes a non-deflectable portion and a deflectable portion. The steerable sheath includes a first pull wire positioned along a first helical path around the circumference of the inner liner from a proximal end to a distal end of the non-deflectable portion of the inner liner and along a first straight path from a proximal end of the deflectable portion to a distal end of the deflectable portion. The steerable sheath includes a second pull wire positioned along a second helical path around the circumference of the inner liner from the proximal end to the distal end of the non-deflectable portion and along a second straight path from the proximal end of the deflectable portion to the distal end of the deflectable portion.

20 Claims, 10 Drawing Sheets

(52) U.S. Cl.
CPC ....... *A61M 25/005* (2013.01); *A61M 25/0045* (2013.01); *A61M 25/0138* (2013.01); *A61M 2025/015* (2013.01); *B29C 65/00* (2013.01)

(58) Field of Classification Search
CPC ......... A61M 25/0138; A61M 2025/015; Y10T 428/1393
USPC ......................................................... 604/95
See application file for complete search history.

(56) References Cited

U.S. PATENT DOCUMENTS

| | | | |
|---|---|---|---|
| 8,734,699 | B2 | 5/2014 | Heideman et al. |
| 2007/0299424 | A1 | 12/2007 | Cumming et al. |
| 2016/0001038 | A1* | 1/2016 | Romo ............... A61M 25/0012 604/526 |
| 2016/0374541 | A1 | 12/2016 | Agrawal et al. |
| 2017/0043129 | A1* | 2/2017 | Fuentes ............. A61M 25/0052 |

* cited by examiner

TORQUEABLE STEERABLE SHEATHS

CROSS-REFERENCE TO RELATED APPLICATIONS

This application claims the benefit of priority to U.S. Provisional Patent Application No. 62/486,725, filed Apr. 18, 2017, entitled "TORQUEABLE STEERABLE SHEATHS," the entire disclosure of which is hereby incorporated by reference herein.

BACKGROUND OF THE DISCLOSURE a. Field of the Disclosure

The present disclosure relates to steerable introducers and methods of making and using steerable introducers. More particularly, the present invention relates to the torqueable steerable sheaths for steerable introducers and methods of making and using such sheaths.

b. Background Art

Steerable introducers are often used for the delivery of medical devices, such as catheters, to a target site. Typically, the sheath of the steerable introducer is manipulated through the patient's vasculature and to the intended site, for example, a site within the patient's heart or other organ, with a medical device, such as a catheter, within a lumen of the sheath. The medical device, or a portion thereof, is advanced out of the sheath for use at the target site.

Steerable sheaths for steerable introducers are typically steered by use of pull wires embedded in the sheath on opposite sides of the sheath. In some known sheaths, the pull wires extend parallel to each other in a straight line from a proximal end of the sheath near the handle of the steerable introducer to a distal end of the sheath. The pull wires are fixedly coupled to the sheath at the distal end of the sheath. Pulling one of the pull wires toward the proximal end of the sheath shortens that pull wire causing a deflectable portion of the distal end of the sheath to deflect in the direction of the shortened wire.

SUMMARY OF THE DISCLOSURE

The present disclosure is directed to a steerable sheath having a proximal end and a distal end. The steerable sheath includes an inner liner having an outer circumference and extending from the proximal end to the distal end of the steerable sheath. The inner liner includes a non-deflectable portion having a proximal end and a distal end, the non-deflectable portion extending from the proximal end of the steerable sheath toward the distal end of the steerable sheath. The inner liner also includes a deflectable portion extending the proximal end adjacent the distal end of the non-deflectable portion to a distal end at the distal end of the steerable sheath. The steerable sheath includes a first pull wire positioned along a first helical path around the circumference of the inner liner from the proximal end to the distal end of the non-deflectable portion of the inner liner and along a first straight path from the proximal end of the deflectable portion to the distal end of the deflectable portion. The steerable sheath includes a second pull wire positioned along a second helical path around the circumference of the inner liner from the proximal end to the distal end of the non-deflectable portion and along a second straight path from the proximal end of the deflectable portion to the distal end of the deflectable portion.

The present disclosure is also directed to a steerable introducer including a handle assembly and a steerable sheath. The steerable sheath is operatively coupled to the handle assembly. The steerable sheath has a proximal end, a distal end, a non-deflectable portion adjacent the proximal end of the steerable sheath, a deflectable portion adjacent the distal end of the steerable sheath, a first pull wire extending from the proximal end to the distal end of the steerable sheath, and a second pull wire extending from the proximal end to the distal end of the steerable sheath. The first pull wire is positioned along a first helical path through the non-deflectable portion of the steerable sheath, and along a first straight path through the deflectable portion of the steerable sheath. The second pull wire is positioned along a second helical path through the non-deflectable portion of the steerable sheath, and along a second straight path through the deflectable portion of the steerable sheath.

The present disclosure is further directed to a method of producing a steerable sheath. The method includes positioning first pull wire along a first helical path around a circumference of a non-deflectable portion of an inner liner from a proximal end of the non-deflectable portion of the inner liner to a distal end of the non-deflectable portion of the inner liner and positioning first pull wire along a first straight path from a proximal end of a deflectable portion of the inner liner to a distal end of the deflectable portion, wherein the proximal end of the deflectable portion of the inner liner is adjacent the distal end of the non-deflectable portion of the inner liner. The method further includes positioning a second pull wire along a second helical path around the circumference of the non-deflectable portion of the inner liner from the proximal end of the non-deflectable portion of the inner liner to the distal end of the non-deflectable portion of the inner liner and positioning the second pull wire along a second straight path from the proximal end of the deflectable portion of the inner liner to the distal end of the deflectable portion of the inner liner.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Steerable introducers may include pull wires extending along a length of the introducer's steerable sheath from a proximal end of the sheath to a distal end of the sheath. As used herein, "proximal" refers to a direction toward the end of the introducer or sheath near the clinician and "distal" refers to a direction away from the clinician and (generally) inside the body of a patient. The pull wires are positioned on opposite sides of the steerable sheath and each runs in a generally straight line from the proximal end to the distal end of the steerable sheath. In use, one of the pull wires is shortened (e.g., pulled toward the proximal end of the steerable introducer) to place it under tension to cause a deflectable portion at the distal end of the steerable sheath to deflect in the direction of the tensioned pull wire. If the operator applies a torque to the introducer to cause the sheath to rotate along its central axis when one of the pull wires is under tension, the pull wires are rotated around the deflected portion of the sheath. The pull wire that is not under tension will need to shorten as it is rotated from an outside of the deflected portion (e.g., from an outer radius of a curve) to an inside of the deflected portion (e.g., to an inner radius of the curve) or the deflected portion of the sheath will change its deflection. Similarly, the tensioned pull wire needs to lengthen as it is rotated by the torque from the inside of the deflected portion to the outside of the deflected portion to maintain the same deflection of the sheath. During such an application of torque to the steerable introducer, energy is stored in the pull wires as the rotation of the sheath attempts to force them to change their lengths. This stored energy may release suddenly, causing the distal end of the steerable shear to make a sudden, fast, and unpredictable movement, sometimes referred to as whipping. At other times, the stored energy may cause one or both of the pull wires to break, typically at their anchor points within the handle of the steerable introducer.

Accordingly, the present disclosure is directed to a steerable sheath including pull wires configured to permit the application of torque to the introducer with the steerable sheath in a deflected position while reducing the likelihood of breaking the pull wires and/or whipping of the distal end of the steerable sheath.

The systems and methods described herein provide a steerable sheath having pull wires that are wrapped around the circumference of the steerable sheath as they extend along the length of a non-deflectable portion of the steerable sheath. Rather than extending in a straight line from proximal end to distal end of the steerable sheath, the pull wires are disposed in a non-overlapping, helical pattern from the proximal end of the sheath to the distal end of the non-deflectable section of the sheath. In the deflectable section of the sheath, the pull wires are disposed in straight lines on opposite sides of the sheath from the proximal end of the deflectable section to the distal end of the deflectable section. The rotation of the pull wires along the length of the non-deflectable section reduces the energy stored in the pull wires when torque is applied to the steerable introducer while the deflectable section is in a deflected position. This allows a smooth, approximately one-to-one response of the steerable introducer to an applied torque without breaking the pull wires or whipping the distal end of the sheath.

Although described herein with respect to a steerable sheath as part of a steerable introducer, the teachings of the present disclosure may be applied to other steerable shafts, and particularly to other steerable medical devices. For example, the pull wire arrangements described herein may be applied to steerable catheters and intracardiac echocardiography catheters.

Figure 1:
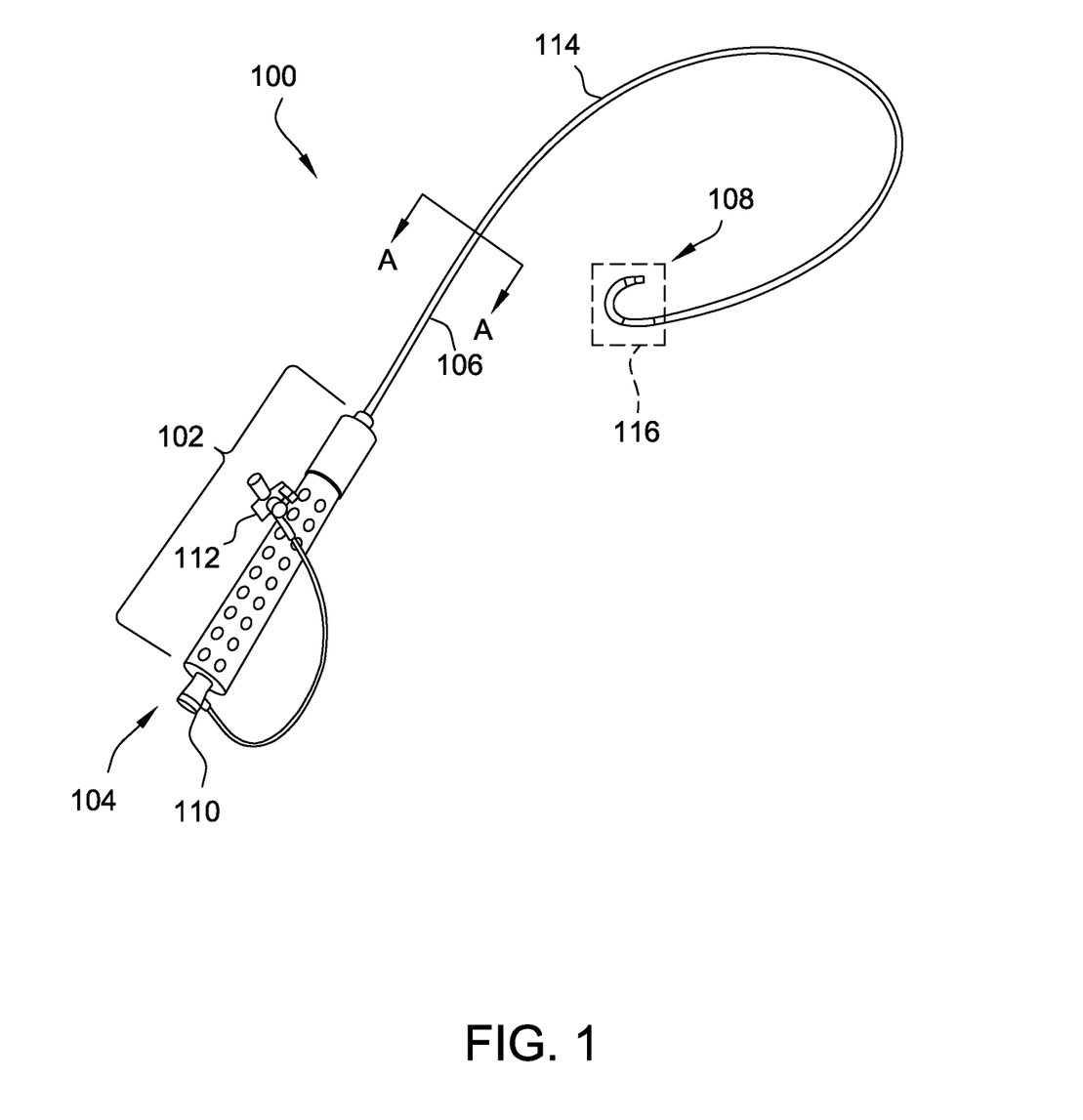
FIG. 1 is a perspective view of one embodiment of a steerable introducer assembly.

Referring now to the Figures, FIG. 1 is a perspective view of a steerable introducer assembly 100 according to one embodiment. Introducer assembly 100 includes a handle assembly 102 at a proximal end 104 and a steerable sheath 106 extending to a distal end 108 of steerable introducer assembly 100. Steerable sheath 106 is operably coupled to handle assembly 102, which assists in guiding or steering steerable sheath 106 during procedures. Introducer assembly 100 further includes a hub 110 operably connected to an inner lumen (not shown) within handle assembly 102 for insertion or delivery of catheter assemblies, fluids, or any other devices known to those of ordinary skill in the art. Optionally, introducer assembly 100 further includes a valve 112 operably connected to hub 110. Steerable sheath 106 includes a flexible, non-deflectable portion 114 and a deflectable portion 116. Non-deflectable portion 114 extends from handle assembly 102 to deflectable portion 116. Deflectable portion 116 is configured to be controllably deflectable by an operator of introducer assembly 100 using pull wires (not shown in FIG. 1) extending through steerable sheath 106 from deflectable portion 116 to handle assembly 102. Components within sheath 106 (discussed below) in non-deflectable portion 114 and deflectable portion 116 may also be referred to as having corresponding non-deflectable and/or deflectable portions. Additional details of the construction and operation of a handle suitable for use as handle assembly 102 are described in U.S. Pat. No. 7,691,095, which is incorporated herein by reference in its entirety. In other embodiments, any other handle suitable for operating steerable sheath 106 may be used as handle assembly 102.

Figure 2:
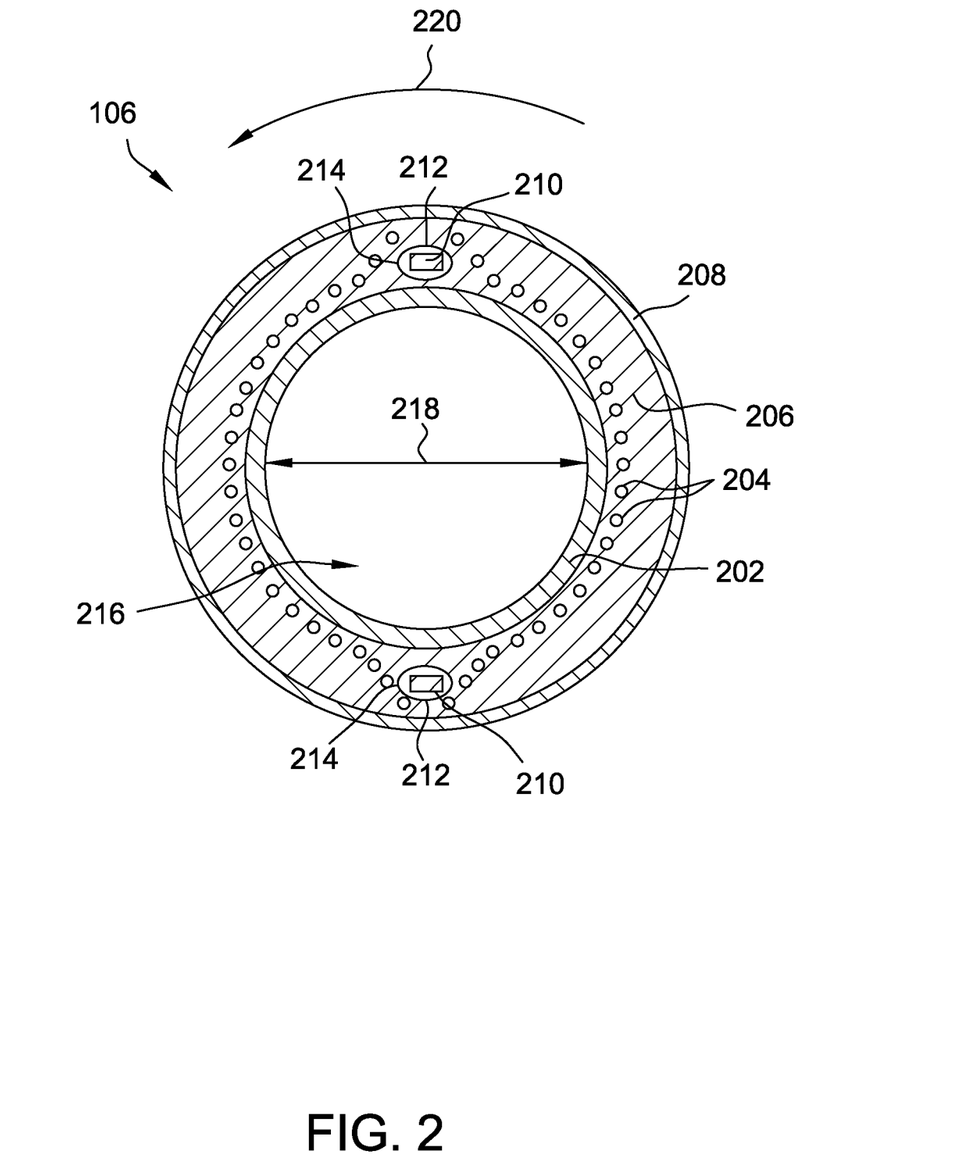
FIG. 2 is a cross section of a steerable sheath of the steerable introducer assembly shown in FIG. 1.

FIG. 2 is a cross-sectional view of steerable sheath 106 taken along the line A-A shown in FIG. 1. Steerable sheath 106 is comprised of a tubular inner liner 202 (also sometimes referred to as an "inner jacket"), a torque transfer layer 204, an outer sheath 206, a heat shrink layer 208, and pull wires 210. In other embodiments, the components of steerable sheath 106 may have different positions relative to each other component. For example, torque transfer layer 204 may be positioned radially inward of pull wires 210. In some embodiments, pull wires 210 are positioned directly adjacent inner liner 202.

Steerable sheath 106 is manufactured using a reflow bonding process. Reflow bonding processes suitable for forming steerable sheath 106 are described in U.S. Pat. Nos. 7,914,515 and 8,734,699, which are incorporated herein by reference in their entireties. In other embodiments, any other suitable method for manufacturing steerable sheath 106 may be used. Heat shrink layer 208 is removed from steerable sheath 106 after a reflow process.

In the example embodiment, pull wires 210 are flat wires. For purposes of this disclosure, a "flat wire" refers to a wire that is characterized by a cross-section that, when measured along two orthogonal axes, is substantially flat. A flat wire typically has a rectangular cross section, though the cross section need not be perfectly rectangular. For example, the present disclosure contemplates that a cross section of the flat wire may be oval, provided that the overall cross section is generally flat. As the term is used herein, a wire may be properly characterized as a flat wire if it has a cross section that is measured x in one direction and at least $2x$ in a second direction generally orthogonal to the first direction. A wire whose cross section is substantially I-shaped may also be a flat wire if, generally, its height is substantially greater than its width at its widest measurement. In other embodiments, pull wires 210 are round wires or wires of any other shape suitable for use as described herein.

Pull wire 210 is preferably about 0.002" by about 0.016", and more preferably about 0.004" by about 0.012" or 0.016". Pull wire 210 may be selected such that the ratio of the width to thickness is at least about 2:1.

In the example embodiment, pull wires 210 are stainless steel wires. In other embodiments, pull wires 210 may be made of any other suitable material, such as spring steel, Nitinol (nickel titanium alloy), or a nickel-cobalt base alloy. A suitable nickel-cobalt base alloy includes MP35N®, which is a registered trademark of SPS Technologies. Inc., of Jenkintown, Pa., USA.

In the example embodiment, pull wires 210 are encased inside another polymeric tubular member 212 forming a lumen 214 for housing the pull wire 210. Polymeric tubular member 212 need not be the same shape as the cross section of pull wire 210, but instead, may be round, oval, rectangular, or another like shape. Preferably, polymeric tubular member 212 has a cross section that is not the same shape as a cross section of pull wire 210, in order to facilitate movement of pull wire 210 in the preformed tube.

In the example embodiments, two pull wires 210 are used in steerable sheath 106. As described in more detail below, pull wires 210 rotate around a circumferential direction 220 of steerable sheath 106 as they extend along the non-deflectable portion 114 of steerable sheath 106. At any point along steerable sheath 106, pull wires 210 remain spaced at about 180 degrees apart. Pull wires 210 extend in straight lines 180 degrees apart through deflectable portion 116 (shown in FIG. 1) without wrapping around sheath 106 in circumferential direction 220. This results in a steerable sheath 106 that can be deflected in two opposite directions by coordinated manipulation of the pull wires 210. In other embodiments, four pull wires located 90 degrees apart may be used to provide four directions of deflectability. In still other embodiments, any suitable number of pull wires may be used to provide a desired number of deflection directions for steerable sheath 106.

Figure 8:
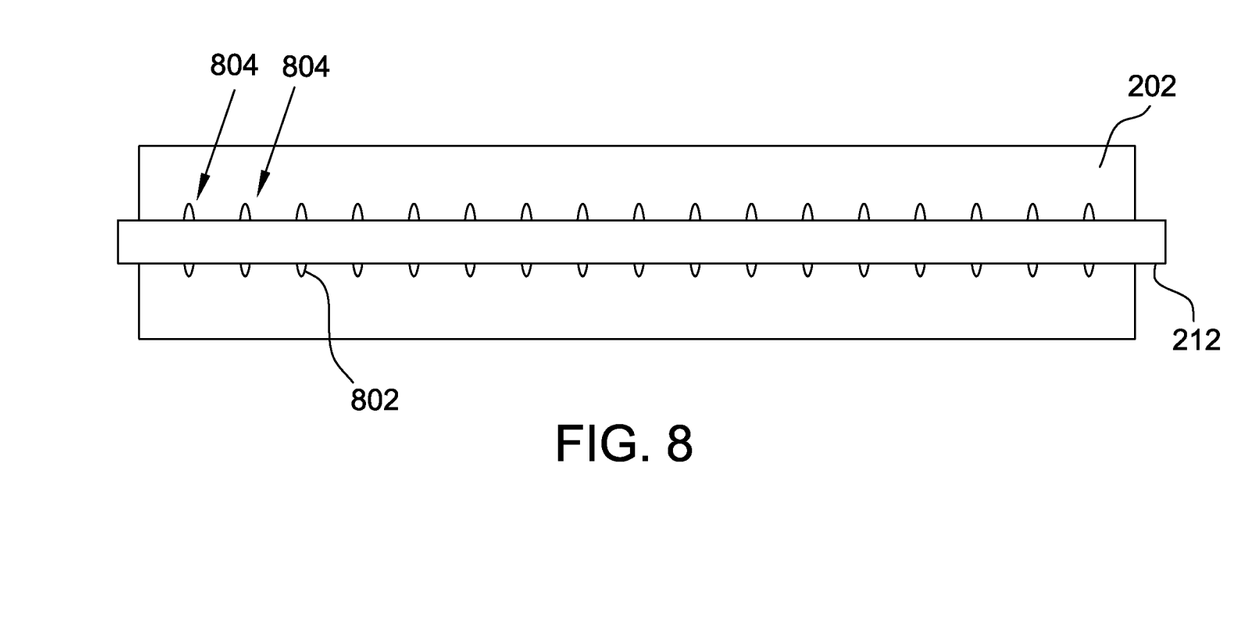
FIG. 8 is a side view of a steerable sheath inner liner illustrating a method of attaching a tubular member to the inner liner.

With reference to FIG. 8, a method of attaching polymeric tubular member 212 to inner liner 202 is depicted. In the illustrated embodiment, adhesive 802 is applied at a plurality of adhesive locations 804. Polymeric tubular member 212 is coupled to inner liner 202 by compressing polymeric tubular member 212 against adhesive 802. Such an attachment method is labor-intensive and, in some cases, may not result in complete coupling of polymeric tubular member 212 to inner liner 202. Moreover, such an attachment method increases in complexity when polymeric tubular members 212 are attached to inner liner 202 in a helical arrangement to accommodate the helical path of pull wires 210.

Figure 9A:
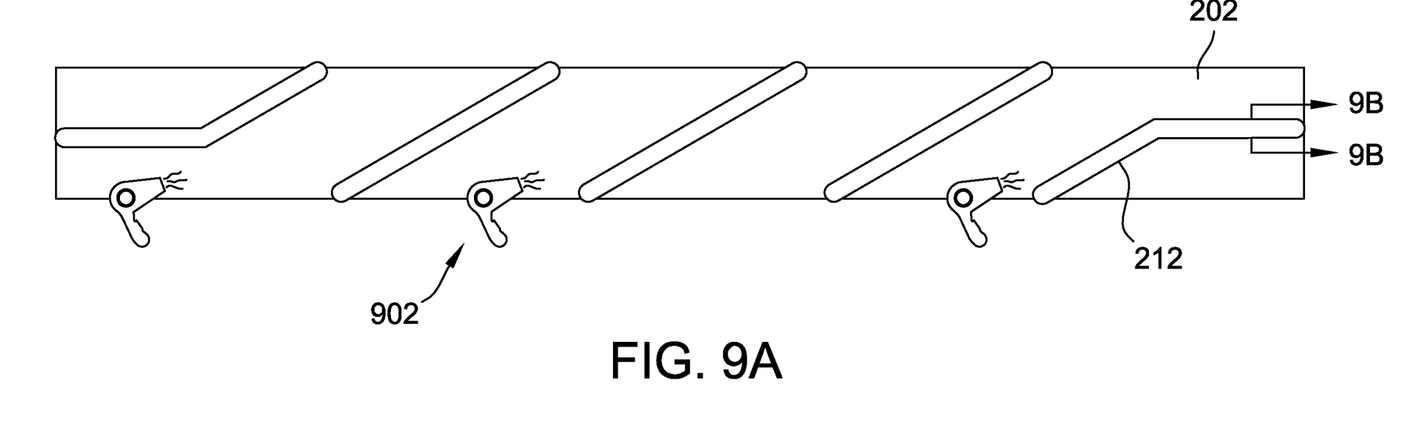
FIG. 9A is a side view of a steerable sheath inner liner illustrating a method of attaching a tubular member to the inner liner using a hot air component.
Figure 9B:
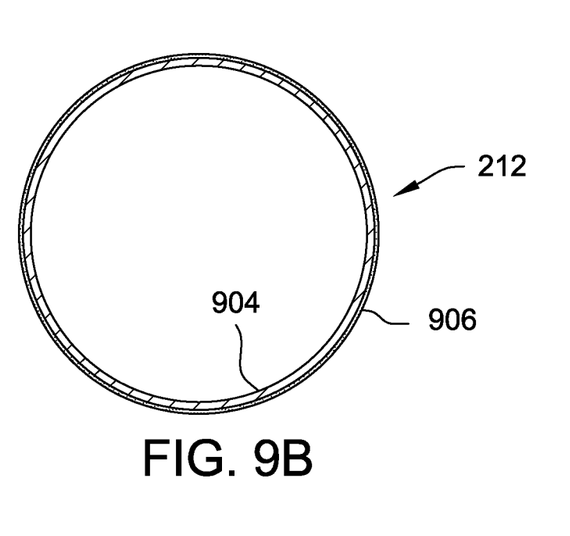
FIG. 9B is a cross-section of the tubular member shown in FIG. 9A.

With reference now to FIGS. 9A and 9B, polymeric tubular member 212 is instead attached to inner liner 202 using a hot air component, indicated generally at 902. As shown in FIG. 9B, polymeric tubular member 212 includes in inner layer 904 and an outer layer 906 surrounding inner layer 904. In the example embodiment, inner layer 904 is preferably polytetrafluoroethylene (PTFE) or etched PTFE, and outer layer 906 is preferably a thermoplastic elastomer, such as Pebax® made by Arkema, Inc. Hot air component 902 is configured to apply hot air to polymeric tubular member 212, thereby melting outer layer 906. The melted outer layer 906 acts as adhesive to bond polymeric tubular member 212 to inner liner 202. The entirety of outer layer 906 may be melted to ensure bonding of polymeric tubular member 212 to inner liner 202 across an entire length of polymeric tubular member 212. Moreover, inner layer 904 preferably has a higher melting point than outer sheath 206 so that inner layer 904 will not melt when hot air component 902 applies heat thereto, nor when steerable sheath 106 is subjected to reflow melt processing.

In other embodiments lumen 214 is not formed using polymeric tubular member 212. Rather, pull wires 210 may be covered with lubricious materials (not shown) before placement, including silicone and other lubricious materials, and lumen 214 may be formed by the presence of pull wires 210 during the reflow process.

Pull wires 210 are connected to at least one steering ring (not shown in FIG. 2) typically located near the distal end 108 (shown in FIG. 1) of steerable introducer assembly 100. The proximal ends of pull wires 210 are operably connected to a steering mechanism (not shown) in handle assembly 102 allowing for manipulation, or steering, of steerable sheath 106 during use. Additional details of the construction and operation of steering rings and steering mechanisms suitable for use in steerable introducer assembly 100 are described in U.S. Patent Application Publication No. 2007/0299424, and U.S. Pat. Nos. 7,691,095, 7,914,515 and 8,734,699, each of which is incorporated herein by reference in its entirety.

Inner liner 202 is preferably a polymeric material, such as polytetrafluoroethylene (PTFE) or etched PTFE. Inner liner 202 may also be made of other melt processing polymers, including, without limitation, polyether block amides, nylon and other thermoplastic elastomers, such as Pebax. Pebax of various durometers may also be used, including without limitation, Pebax 30D to Pebax 70D. In a preferred embodiment, inner liner 202 is made of a material with a melting temperature higher than outer sheath 206 such that inner liner 202 will withstand the melt processing of the outer sheath 206.

Inner liner 202 defines a lumen 216 therethrough for receiving an elongate medical device, such as a catheter. Lumen 216 preferably has a diameter 218 of at least about 6 French, more preferably of at least about 7 French, and most preferably of between about 10 French and about 24 French. However, in some embodiments, it is contemplated that lumen 216 may have a diameter 218 of up to about 32 French or more, such as between about 7 French and about 32 French.

Torque transfer layer 204 is disposed between inner liner 202 and heat shrink layer 208, and more preferably between outer sheath 206 and inner liner 202. Torque transfer layer 204 may be made of stainless steel (304 or 316) wire or other acceptable materials known to those of ordinary skill in the art. Torque transfer layer 204 is preferably formed of a braided wire assembly comprised of flat wires, preferably stainless steel wires including, for example, high tensile stainless steel wires. Torque transfer layer 204 may be formed in any number of known braid patterns, including one-over-one (involving at least two wires) or two-over-two (involving at least four wires) crossover patterns. For lumen diameters of at least about 6 French, braided flat wires of at least about 0.003" thick by at least about 0.007" wide may be used. In general, the individual wires have a ratio of width to the thickness of at least about 2:1, including, for example, 2:1 to 5:1. Flat wires of about 0.004" thick by about 0.012" wide and of about 0.004" thick by about 0.020" wide have also been braided with success to form torque transfer layers of superior performance.

Outer sheath 206 is preferably either an extruded Pebax or PTFE tubing. The melt-processing polymer of outer sheath 206 occupies a plurality of voids of the wire mesh in torque transfer layer 204. Outer sheath 206 may also be made of other melt processing polymers, including, without limitation, etched PTFE, polyether block amides, nylon and other thermoplastic elastomers, at varying durometers. Outer sheath 206 may also comprise more than one layer, including, for example, two or more tubes of a melt processing polymer. Alternatively, outer sheath 206 may be comprised of varying segments (not shown) differing in hardness and/or material along the length of steerable sheath 106 and being reflow bonded together. Varying the sheath composition in this manner provides the additional benefit of adjusting flexibility, torqueability, and pushability at various points along steerable sheath 106.

Figure 3:
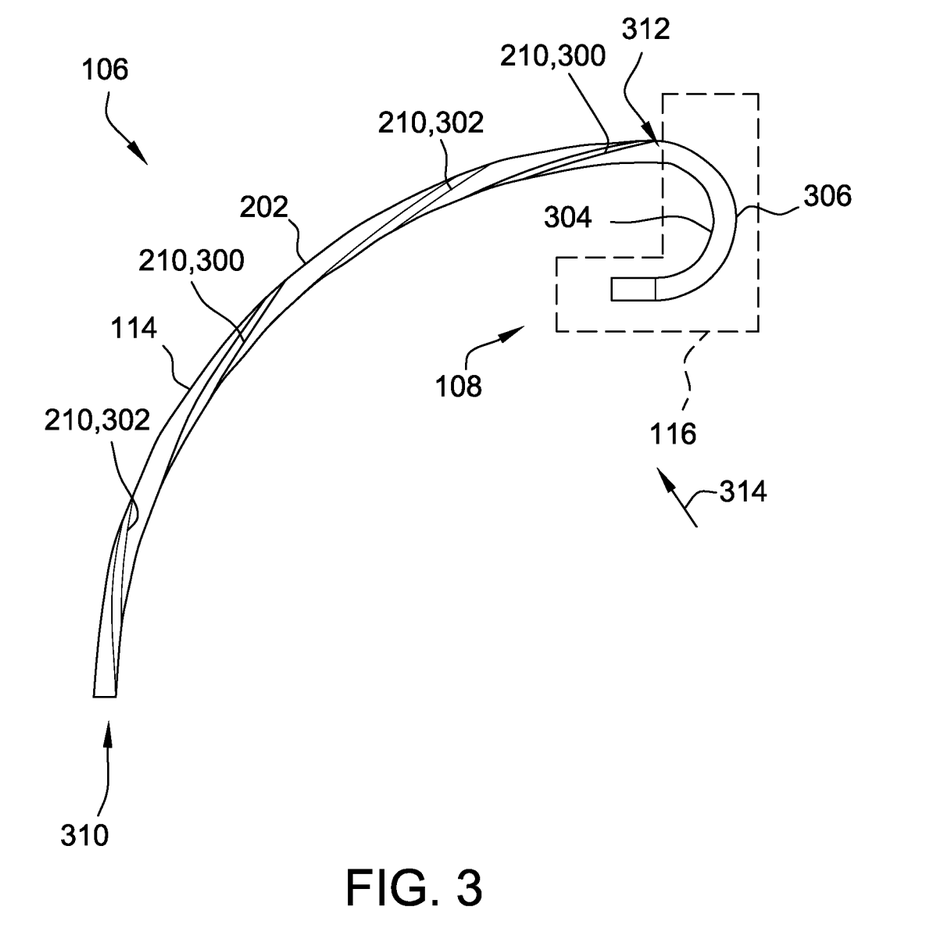
FIG. 3 is a side view of the steerable sheath shown in FIG. 2 with outer layers removed to show the sheath's embedded pull wires.
Figure 4:
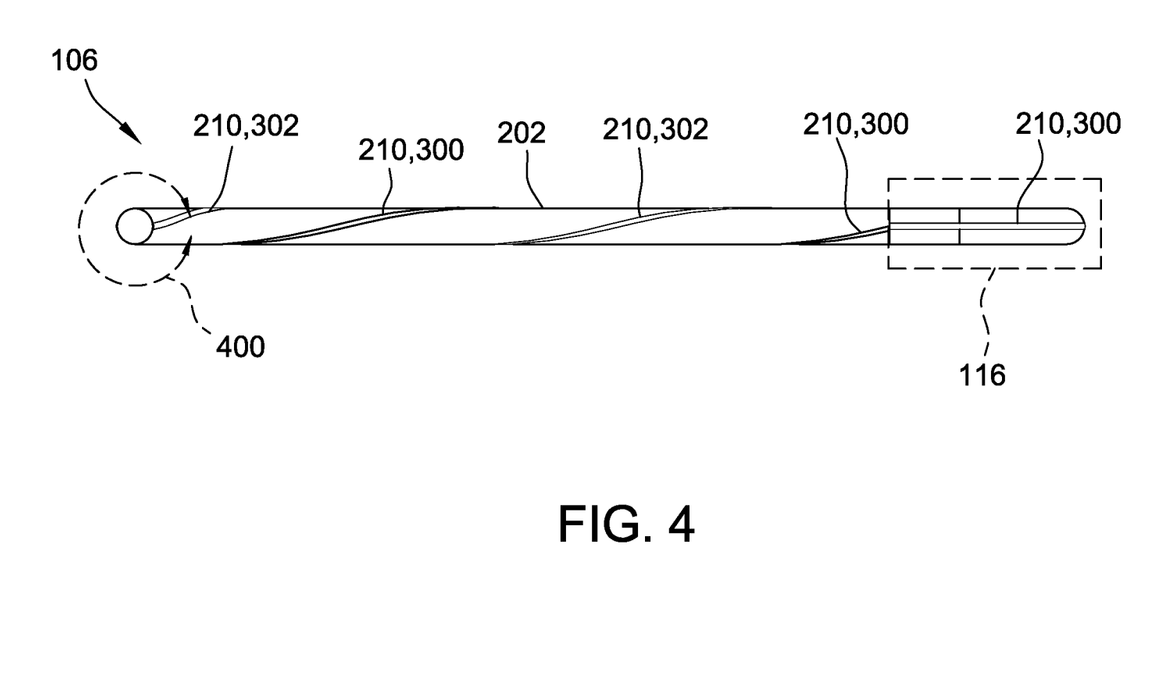
FIG. 4 is a top view of the steerable sheath as shown in FIG. 3.
Figure 5:
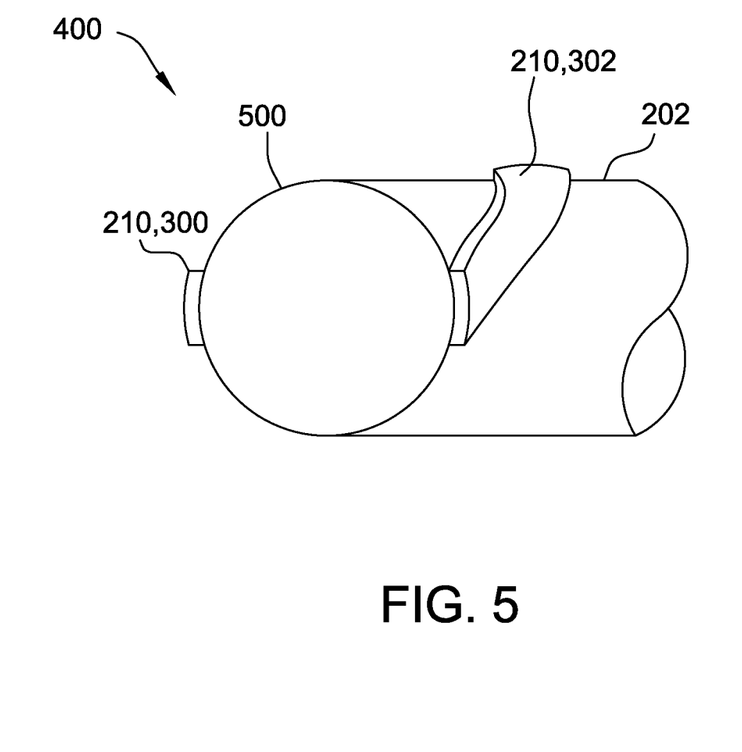
FIG. 5 is a perspective view of a section of the steerable sheath as shown in FIG. 4.

FIGS. 3, 4, and 5, are various views of steerable sheath 106 with torque transfer layer 204, outer sheath 206, and heat shrink layer 208 removed. FIG. 3 is a side view of steerable sheath 106. FIG. 4 is a top view of steerable sheath 106 in the same configuration as seen from direction 314 shown in FIG. 3. FIG. 5 is an enlarged view of a section 400 of steerable sheath 106 shown in FIG. 4.

Pull wires 210 are separately identified in FIGS. 3, 4, and 5 as first pull wire 300 and second pull wire 302. As shown in FIG. 3, deflectable portion 116 is deflected to a U-shape having an inner radius 304 and an outer radius 306. Pull wires 210 extend from a proximal end 310 of steerable sheath 106 to distal end 108.

In non-deflectable portion 114, first pull wire 300 and second pull wire 302 wrap around inner liner 202. Inner liner 202 is a cylindrical tube having an outer circumference 500 (shown in FIG. 5). In non-deflectable portion 114, first pull wire 300 and second pull wire 302 traverse around circumference 500 of inner liner 202 as they extend from proximal end 310 toward distal end 108. Thus, in non-deflectable portion 114, each pull wire 210 follows a substantially helical path from proximal end 310 to distal end 108. First pull wire 300 and second pull wire 302 both wrap around inner liner 202 at a same rate (e.g., number of rotations per unit of length) and do not cross over each other. The helical path followed by first pull wire 300 is offset from the helical path followed by second pull wire by 180 degrees around the circumference 500 (i.e., in a circumferential direction) of inner liner 202. Thus, first pull wire 300 and second pull wire 302 remain substantially 180 degrees apart throughout non-deflectable portion 114.

In the example embodiment, first pull wire 300 and second pull wire 302 are each wrapped twice (i.e., 720 degrees or two revolutions) around inner liner 202 as they traverse non-deflectable portion 114 from proximal end 310 toward distal end 108. In other embodiments, pull wires 300, 302 may wrap around inner liner 202 a different number of times. As the number of revolutions about inner liner 202 increases, torqueability of steerable sheath 106 without whipping or breaking pull wires 210 generally increases. However, friction along pull wires 210 may also increase with increased revolutions, leading to greater force being necessary to deflect deflectable portion 116. Moreover, increasing the number of times each pull wire 210 wraps about inner liner 202 increases the length of pull wires 210, thereby potentially increasing material costs. Preferably, each pull wire 210 makes between one and four revolutions around inner liner 202 in non-deflectable portion 114. In some embodiments, each pull wire 210 makes between one and three revolutions around inner liner 202 in non-deflectable portion 114. In some embodiments, each pull wire 210 makes between one and two revolutions around inner liner 202.

During assembly of steerable sheath 106, first pull wire 300 and second pull wire 302 may be bonded to inner liner 202 to hold them in place until the reflow process is performed. In embodiments that include polymeric tubular member 212 to form lumen 214 (both shown in FIG. 2), polymeric tubular member 212 may be bonded to inner liner 202.

In the example embodiment, first pull wire 300 and second pull wire 302 are wrapped around inner liner 202 in a counter-clockwise manner (as viewed from proximal end 310). In other embodiments, first pull wire 300 and second pull wire 302 wrap around inner liner 202 in a clockwise manner (as viewed from proximal end 310).

In deflectable portion 116, first pull wire 300 and second pull wire 302 do not wrap around inner liner 202. Rather, first pull wire 300 and second pull wire 302 each traverse a substantially straight path from a proximal end 312 of deflectable portion 116 to distal end 108. Although not visible in FIG. 3, first pull wire 300 continues from proximal end 312 of deflectable portion 116 to distal end 108 along outer radius 306. Similarly, second pull wire 302 continues from proximal end 312 of deflectable portion 116 to distal end 108 along inner radius 304. In FIG. 4, first pull wire 300 can be seen traversing a straight path along a portion of outer radius 306 in deflectable portion 116.

Although first pull wire 300 and second pull wire 302 are illustrated as ending at proximal end 310, it should be understood that first pull wire 300 and second pull wire 302 may extend beyond inner liner 202 in the proximal direction to permit access (such as by handle assembly 102, shown in FIG. 1) to first pull wire 300 and second pull wire 302 for operation of steerable sheath 106.

Figure 6:
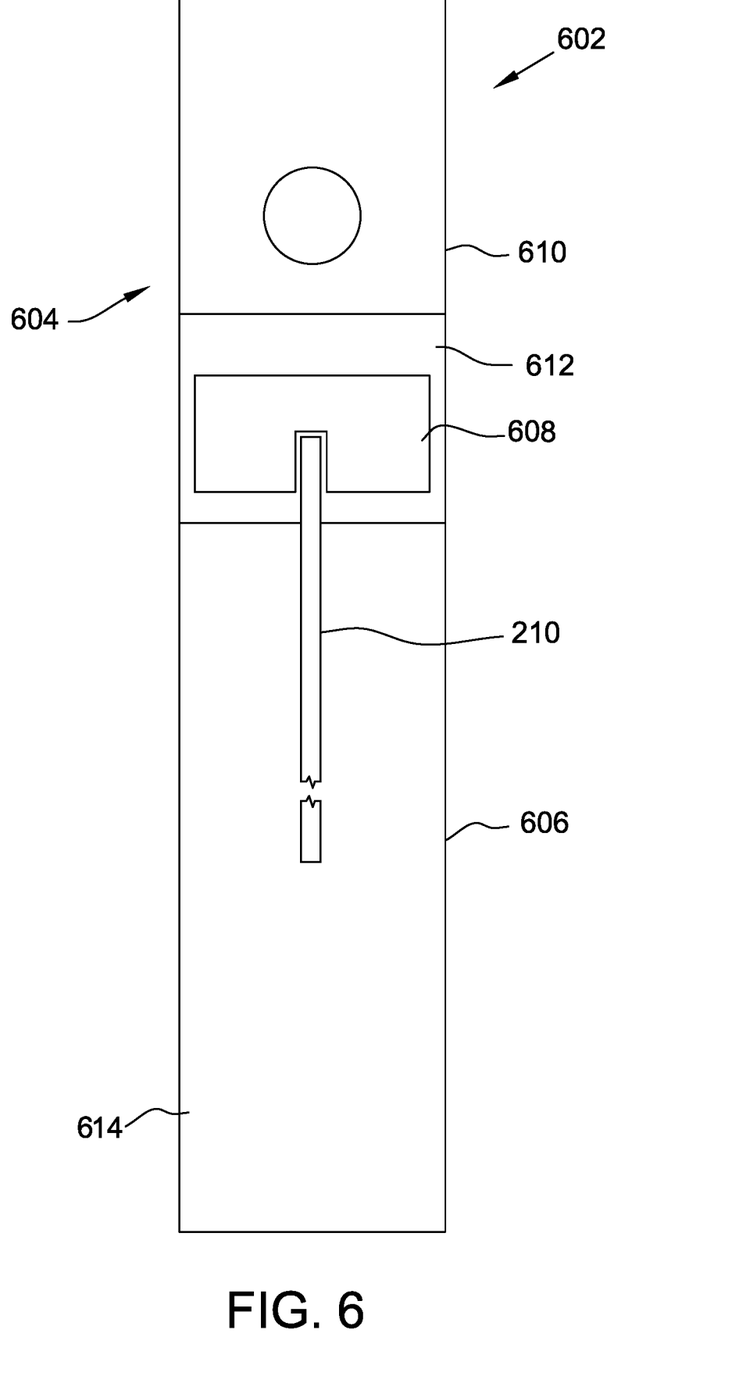
FIG. 6 is a cross-section of another embodiment of a steerable sheath of the steerable introducer assembly shown in FIG. 1.

FIG. 6 is a cross-section of another embodiment of a steerable sheath 602 of steerable introducer assembly 100 (shown in FIG. 1). Specifically, a distal portion 604 of steerable sheath 602 is shown. Steerable sheath 602 may be substantially similar to steerable sheath 106 (shown in FIG. 1). In the illustrated embodiment, steerable sheath 602 includes a shaft 606 circumscribing a pull ring or steering ring 608 coupled to at least one pull wire 210. Although only one pull wire 210 is illustrated in the view of FIG. 6, as described above, steerable sheath 602 may include two pull wires 210 in a helical arrangement along at least a portion of sheath 602 and/or in a straight line along at least a portion of sheath 602, about 180 degree apart.

A distal tip 610 of shaft 606 is relatively soft or low-durometer, to minimize the risk of tissue damage upon impact of distal tip 610 with any tissue in a patient's vasculature. In the illustrated embodiment, an intermediate segment 612 of distal portion 604 provided around pull ring 608 is relatively hard or high-durometer. As tension in pull wire 210 is increased to deflect at least a portion of shaft 606, a relatively high load is experienced at intermediate segment 612 provided around pull ring 608. Accordingly, increasing the hardness of intermediate segment 612 facilitates intermediate segment 612 withstanding these increased loads. A body segment 614 of shaft 606 is relatively flexible to allow flexion thereof. Body segment 614 may extend from a deflectable portion (e.g., deflectable portion 116, shown in FIG. 1) to a non-deflectable portion (e.g., non-deflectable portion 114, also shown in FIG. 1) of steerable sheath 602, from distal portion 604 to a proximal end (not shown) of steerable sheath 602, or along any suitable portion of steerable sheath 602.

Figure 7A:
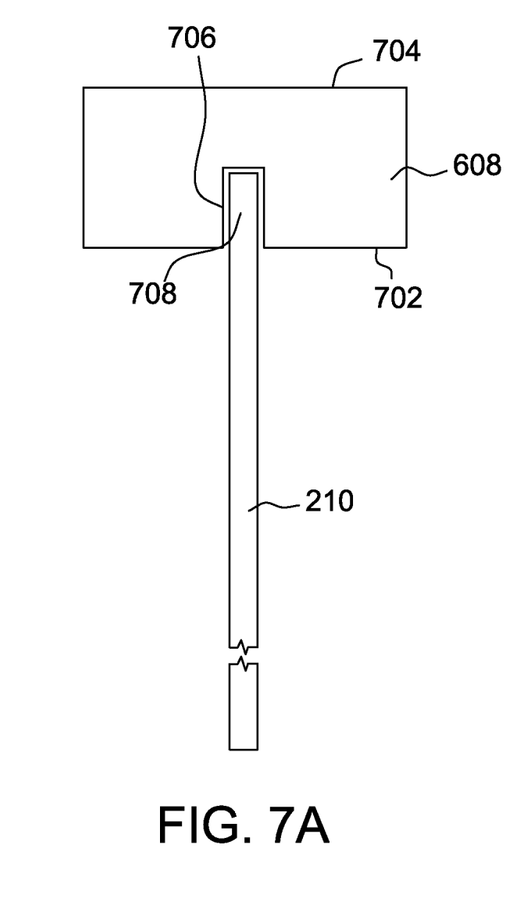
FIG. 7A illustrates an arrangement of a pull ring coupled to a pull wire.

FIG. 7A illustrates an arrangement of pull ring 608 coupled to pull wire 210, as also shown in FIG. 6. Pull ring 608 has a proximal face 702 oriented towards a proximal end (not shown) of a steerable sheath (e.g., steerable sheath 106, shown in FIG. 1, or steerable sheath 602, shown in FIG. 6) in which pull ring 608 is provided. Pull ring 608 also has a distal face 704 opposite proximal face 702. When pull ring 608 is provided within a steerable sheath, the material of the sheath may be bonded with pull ring 608. Specifically, at least a portion of the material of the sheath is bonded with proximal face 702. The strength of the bond at least partially depends on the surface area of the bond (the "bond surface area"). In the illustrated embodiment, proximal face 702 is substantially planar. As such, the bond between pull ring 608 and the steerable sheath in which pull ring 608 is provided limited to the planar surface area of proximal face 702.

In addition, pull ring 608 defines a pocket 706 in which a distal end 708 of pull wire 210 is positioned. Specifically, distal end 708 is coupled (e.g., adhered, welded, fastened, etc.) to pull ring 608 within pocket 706.

Figure 7B:
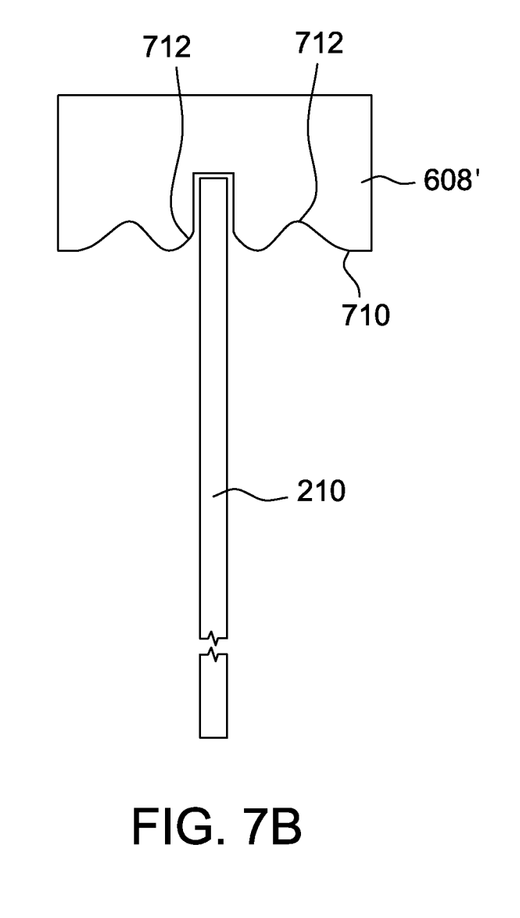
FIG. 7B is a cross-section of a first embodiment of a modified pull ring coupled to a pull wire that may be used in the steerable introducer shown in FIG. 1.

FIG. 7B is a cross-section of a first embodiment of a modified pull ring 608' coupled to pull wire 210. Modified pull ring 608' has a proximal face 710 oriented towards a proximal end (not shown) of a steerable sheath (e.g., steerable sheath 106, shown in FIG. 1, or steerable sheath 602, shown in FIG. 6) in which modified pull ring 608' is provided. Proximal face 710 has an irregular or non-planar shape. In the illustrated embodiment, proximal face 710 includes a plurality of troughs or grooves 712. Grooves 712 may be annular grooves, radial grooves, irregular grooves, and/or have any other shape or orientation. Grooves 712 increase the surface area of proximal face 710. Accordingly, grooves 712 increase the bond surface area when modified pull ring 608' is provided within a steerable sheath. As such, grooves 712 improves the bond strength between the steerable sheath when steerable sheath is bent. In other words, during increased loads (i.e., when pull wires 210 are pulled t deflect modified pull ring 608'), grooves 712 facilitate improved bending at a joint defined between the steerable sheath and proximal face 710 without degradation of the bond at the joint.

Figure 7C:
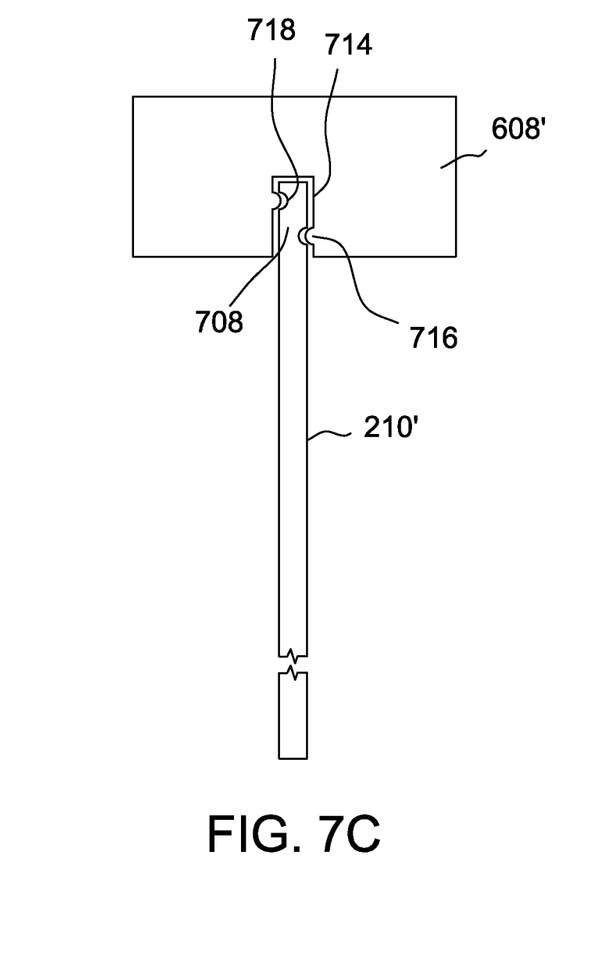
FIGS. 7C and 7D are respective cross-sections of a second and third embodiment of a modified pull ring coupled to a modified pull wire that may be used in the steerable introducer assembly shown in FIG. 1.
Figure 7D:
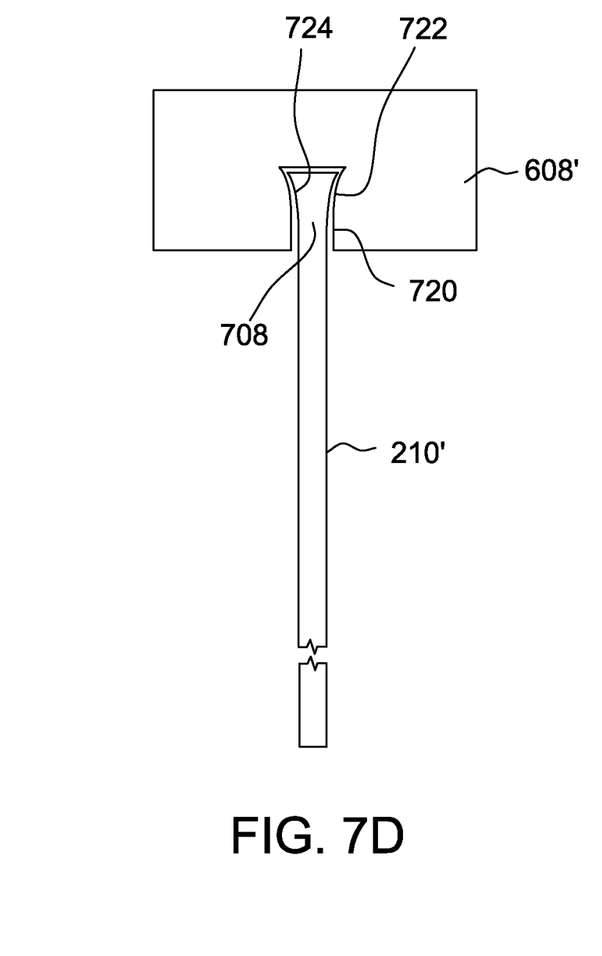

FIGS. 7C and 7D are respective cross-sections of alternative embodiments of a modified pull ring 608' coupled to a modified pull wire 210'. In FIG. 7C, modified pull ring 608' includes a modified pocket 714. Modified pocket 714 includes one or more projections 716 that project radially into modified pocket 714. In addition, modified pull wire 210' defines one or more cutouts 718 in distal end 708 thereof. Each cutout 718 receives a respective projection 716 therein.

In FIG. 7D, modified pull ring 608' includes a modified pocket 720. Modified pocket 720 defines a diameter 722 thereof that increases as modified pocket 720 extends axially inwardly into modified pull ring 608'. In addition, modified pull wire 210' defines a diameter 724 thereof that increases along distal end 708 thereof.

Each of the modified pockets 714, 720 in combination with their respective modified pull wires 210' facilitates further strengthening the bond at the joint defined between modified pull rings 608' and the steerable sheath (e.g., steerable sheath 106, shown in FIG. 1, or steerable sheath 602, shown in FIG. 6) in which the respective modified pull ring 608' is provided. In some embodiments, the modified pockets 714 and/or 720 are combined with proximal face 710 (shown in FIG. 7B) to even further strength the bond at the pull ring-sheath interface.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A steerable sheath having a proximal end and a distal end, the steerable sheath comprising,
   an inner liner having an outer circumference and extending from the proximal end to the distal end of the steerable sheath, the inner liner including:
      a non-deflectable portion having a proximal end and a distal end, the non-deflectable portion extending from the proximal end of the steerable sheath toward the distal end of the steerable sheath;
      a deflectable portion extending from a proximal end adjacent the distal end of the non-deflectable portion to a distal end at the distal end of the steerable sheath;
   a first pull wire positioned along a first helical path around the outer circumference of the inner liner from the proximal end to the distal end of the non-deflectable portion of the inner liner and along a first straight path from the proximal end of the deflectable portion to the distal end of the deflectable portion;
   a first polymeric tubular member positioned along the first helical path and enclosing the first pull wire, the first tubular member having an outer layer and an inner layer, the outer layer and the inner layer made of different materials to facilitate attaching the first tubular member to the inner liner along the first helical path; and a second pull wire positioned along a second helical path around the outer circumference of the inner liner from the proximal end to the distal end of the non-deflectable portion and along a second straight path from the proximal end of the deflectable portion to the distal end of the deflectable portion.

2. The steerable sheath of claim 1, wherein the first helical path and the second helical path each complete two revolutions around the inner liner from the proximal end to the distal end of the non-deflectable portion.

3. The steerable sheath of claim 1, wherein the first pull wire and the second pull wire comprise flat wire.

4. The steerable sheath of claim 1, wherein the first pull wire and the second pull wire are stainless steel pull wires.

5. The steerable sheath of claim 1, wherein the first helical path is offset from the second helical path by 180 degrees around the outer circumference of the inner liner.

6. The steerable sheath of claim 1, wherein the first straight path is offset from the second straight path by 180 degrees around the outer circumference of the inner liner.

7. The steerable sheath of claim 1, further comprising a second polymeric tubular member positioned along the second helical path and enclosing the second pull wire.

8. The steerable sheath of claim 1, wherein the outer layer of the first polymeric tubular member has a lower melting point than the inner layer of the first polymeric tubular member.

9. The steerable sheath of claim 1, wherein the outer and inner layers of the first polymeric tubular member are coaxial with the first pull wire.

10. The steerable sheath of claim 1, wherein the inner layer is positioned between the outer layer and the first pull wire.

11. The steerable sheath of claim 1, wherein the outer layer is a thermoplastic elastomer, and wherein the inner layer is polytetrafluoroethylene (PTFE).

12. A steerable introducer comprising,
a handle assembly,
a steerable sheath operatively coupled to the handle assembly, the steerable sheath having a proximal end, a distal end, a non-deflectable portion adjacent the proximal end of the steerable sheath, a deflectable portion adjacent the distal end of the steerable sheath, a first pull wire extending from the proximal end to the distal end of the steerable sheath, a first polymeric tubular member enclosing the first pull wire, and a second pull wire extending from the proximal end to the distal end of the steerable sheath, wherein:
the first pull wire is positioned along a first helical path through the non-deflectable portion of the steerable sheath, and along a first straight path through the deflectable portion of the steerable sheath;
the first polymeric tubular member is positioned along the first helical path and includes an outer layer and an inner layer, the outer layer and the inner layer made of different materials to facilitate attaching the first tubular member to the inner liner along the first helical path; and
the second pull wire is positioned along a second helical path through the non-deflectable portion of the steerable sheath, and along a second straight path through the deflectable portion of the steerable sheath.

13. The steerable introducer of claim 12, wherein the first helical path and the second helical path each complete two revolutions about the steerable sheath from a proximal end to a distal end of the non-deflectable portion.

14. The steerable introducer of claim 12, wherein the steerable sheath further comprises a second polymeric tubular member positioned along the second helical path and enclosing the second pull wire.

15. The steerable introducer of claim 12, wherein each of the first pull wire and the second pull wire extends from the proximal end of the steerable sheath and are operatively coupled to the handle assembly.

16. A method of producing a steerable sheath comprising:
positioning a first pull wire along a first helical path around a circumference of a non-deflectable portion of an inner liner from a proximal end of the non-deflectable portion of the inner liner to a distal end of the non-deflectable portion of the inner liner;
positioning the first pull wire along a first straight path from a proximal end of a deflectable portion of the inner liner to a distal end of the deflectable portion, wherein the proximal end of the deflectable portion of the inner liner is adjacent the distal end of the non-deflectable portion of the inner liner;
bonding a first polymeric tubular member to the inner liner along the first helical path by applying hot air to the first polymeric tubular member, the first polymeric tubular member including an outer layer and an inner layer, the outer layer and the inner layer made of different materials;
positioning the first pull wire in the first polymeric tubular member;
positioning a second pull wire along a second helical path around the circumference of the non-deflectable portion of the inner liner from the proximal end of the non-deflectable portion of the inner liner to the distal end of the non-deflectable portion of the inner liner; and
positioning the second pull wire along a second straight path from the proximal end of the deflectable portion of the inner liner to the distal end of the deflectable portion of the inner liner.

17. The method of claim 16, wherein positioning the first pull wire along the first helical path comprises positioning the first pull wire along the first helical path that completes two revolutions around the circumference of the inner liner between the proximal end of the non-deflection portion and the distal end of the non-deflectable portion, and positioning the second pull wire along the second helical path comprises positioning the second pull wire along the second helical path that completes two revolutions around the circumference of the inner liner between the proximal end of the non-deflection portion and the distal end of the non-deflectable portion.

18. The method of claim 16, wherein positioning the second pull wire along the second helical path comprises positioning the second pull wire along the second helical path offset from the first helical path by 180 degrees in a circumferential direction around the inner liner.

19. The method of claim 16, further comprising:
bonding a second polymeric tubular member to the inner liner along the second helical path by applying hot air to the second polymeric tubular member, the second polymeric tubular member including an outer layer and an inner layer, the outer layer and the inner layer made of different materials; and positioning the second pull wire in the second polymeric tubular member.

20. The method of claim 16, wherein positioning the second pull wire along the second straight path comprises positioning the second pull wire along the second straight path offset from the first straight path by 180 degrees in a circumferential direction around the inner liner.

\* \* \* \* \*